United States Patent
Levy et al.

(10) Patent No.: US 7,052,498 B2
(45) Date of Patent: May 30, 2006

(54) EXPANDABLE ORTHOPEDIC DEVICE

(75) Inventors: Mark M. Levy, Raanana (IL); Ilan Greenberg, Haifa (IL)

(73) Assignee: Expanding Orthopedics, Inc., Boston, MA (US)

( * ) Notice: Subject to any disclaimer, the term of this patent is extended or adjusted under 35 U.S.C. 154(b) by 90 days.

(21) Appl. No.: 10/349,210

(22) Filed: Jan. 21, 2003

(65) Prior Publication Data
US 2003/0130660 A1 Jul. 10, 2003

Related U.S. Application Data

(63) Continuation of application No. 09/907,514, filed on Jul. 16, 2001, now Pat. No. 6,554,833, which is a continuation-in-part of application No. 09/426,563, filed on Oct. 22, 1999, now Pat. No. 6,261,289.

(60) Provisional application No. 60/105,593, filed on Oct. 26, 1998.

(30) Foreign Application Priority Data
Oct. 19, 2000 (IL) ....................... PCT/IL00/00666

(51) Int. Cl.
*A61B 17/56* (2006.01)

(52) U.S. Cl. .............................. 606/63; 606/62; 606/64

(58) Field of Classification Search ................ 606/63, 606/62, 60, 61, 64, 65, 66, 67, 72, 73; 623/16.11
See application file for complete search history.

(56) References Cited

U.S. PATENT DOCUMENTS

| 2,675,801 | A |   | 4/1954 | Bambara et al. |
|---|---|---|---|---|
| 2,998,007 | A |   | 8/1961 | Herzog |
| 3,710,789 | A |   | 1/1973 | Ersek |
| 3,759,257 | A |   | 9/1973 | Fisher et al. |
| 3,779,239 | A | * | 12/1973 | Fischer et al. ............... 606/63 |
| 4,170,990 | A |   | 10/1979 | Baumgart et al. |
| 4,204,531 | A | * | 5/1980 | Aginsky ..................... 606/63 |
| 4,227,518 | A |   | 10/1980 | Aginsky |
| 4,236,512 | A |   | 12/1980 | Aginsky |

(Continued)

FOREIGN PATENT DOCUMENTS

| DE | 3146065 | * | 5/1983 | ................ 606/63 |
|---|---|---|---|---|

(Continued)

OTHER PUBLICATIONS

European Patent Office Search Report for EP Patent Application No. 04030532.8, Applicant: Levy, Mark, Form EPO 1507.0 (03.95), dated Feb. 24, 2005 (3 pages).

*Primary Examiner*—Pedro Philogene
(74) *Attorney, Agent, or Firm*—Bingham McCutchen LLP

(57) ABSTRACT

A device for stabilizing bone includes a tubular body having first and second end regions defining a longitudinal axis therebetween. A plurality of splines extend from the first end region, the splines including first ends coupled to the first end region, and second ends disposed away from the first end region, the second ends being directable from a generally axial collapsed state to a substantially transverse expanded state. A plurality of support arms are coupled to the splines, and an actuator is coupled to the support arms, the actuator movable axially relative to the elongate body for causing the support arms to direct the second ends of the splines from the collapsed state to the expanded state. Optionally, the device includes another set of splines extending from the second end region or located at an intermediate region of the tubular body.

22 Claims, 10 Drawing Sheets

U.S. PATENT DOCUMENTS

| | | |
|---|---|---|
| 4,313,434 A | 2/1982 | Segal |
| 4,453,539 A | 6/1984 | Raftopoulos et al. |
| 4,502,161 A | 3/1985 | Wall |
| 4,683,878 A | 8/1987 | Carter |
| 4,854,312 A | 8/1989 | Raftopoilos et al. |
| 5,034,013 A | 7/1991 | Kyle et al. |
| 5,057,103 A | 10/1991 | Davis |
| 5,102,413 A | 4/1992 | Poddar |
| 5,116,335 A | 5/1992 | Hannon et al. |
| 5,201,737 A | 4/1993 | Leibinger et al. |
| 5,250,048 A | 10/1993 | Gundolft |
| 5,281,225 A | 1/1994 | Vicenzi |
| 5,380,328 A | 1/1995 | Morgan |
| 5,433,718 A | 7/1995 | Brinker |
| 5,437,674 A * | 8/1995 | Worcel et al. ............... 606/73 |
| 5,458,599 A | 10/1995 | Adobbati |
| 5,468,242 A | 11/1995 | Reisberg |
| 5,658,310 A | 8/1997 | Berger |
| 5,665,089 A | 9/1997 | Dall et al. |
| 5,713,901 A | 2/1998 | Tock |
| 5,766,176 A | 6/1998 | Duncan |
| 5,779,703 A | 7/1998 | Benoist |
| 5,836,949 A | 11/1998 | Campbell, Jr. et al. |
| 5,879,352 A | 3/1999 | Filoso et al. |
| 5,919,194 A | 7/1999 | Anderson |
| 6,554,833 B1 * | 4/2003 | Levy et al. ................. 606/63 |

FOREIGN PATENT DOCUMENTS

| | | | |
|---|---|---|---|
| DE | 39 22 044 A1 | 2/1991 | |
| DE | 3922044 * | 2/1991 | ............... 606/63 |
| DE | 196 12 276 A1 | 10/1997 | |
| EP | 0 553 517 A1 | 8/1993 | |
| EP | 0 566 255 B1 | 10/1993 | |
| EP | 0 713 685 | 11/1995 | |
| EP | 0 738 502 A2 | 4/1996 | |
| EP | 0 738 502 A3 | 4/1996 | |
| EP | 0 882 431 A1 | 6/1998 | |
| EP | 0922437 | 6/1999 | |
| FR | 2653006 * | 4/1991 | ............... 606/63 |
| FR | 2741256 | 5/1997 | |
| GB | 2 268 068 A | 1/1994 | |
| RU | 967478 | 10/1982 | |
| SU | 1049-050 A | 10/1983 | |
| SU | 1109-142 A | 8/1984 | |
| SU | 1250-280 A | 8/1986 | |
| SU | 1623-634 A | 1/1991 | |
| WO | WO 97/01990 | 6/1995 | |
| WO | WO 98/24380 | 12/1996 | |
| WO | WO 97/37606 | 4/1997 | |
| WO | WO 97/38641 | 4/1997 | |
| WO | WO 98/01077 | 7/1997 | |
| WO | WO 98/03124 | 7/1997 | |
| WO | WO 98/23215 | 11/1997 | |
| WO | WO 98/38918 | 3/1998 | |
| WO | WO 98/36699 | 8/1998 | |
| WO | WO 00/44319 | 8/2000 | |
| WO | WO 00/44946 | 8/2000 | |
| WO | WO 0128443 | 4/2001 | |
| WO | WO01/34045 * | 5/2001 | ............... 606/63 |
| WO | WO 0134045 | 5/2001 | |

* cited by examiner

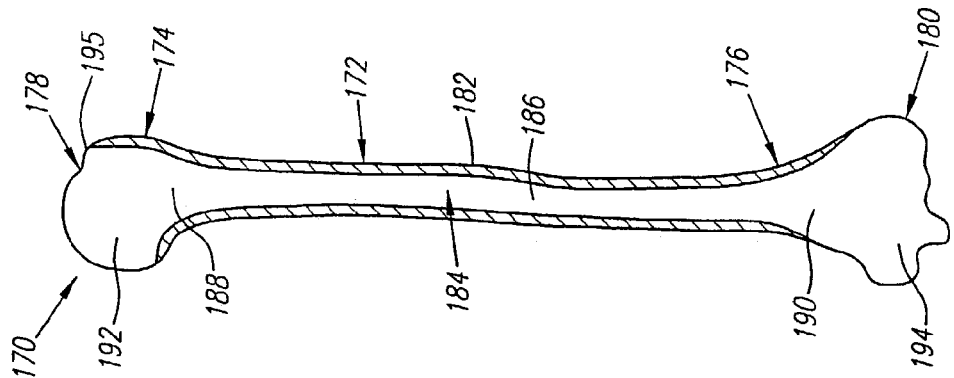
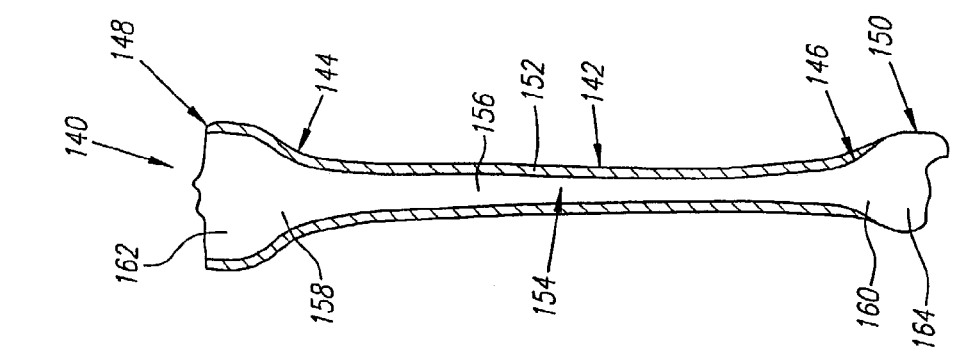
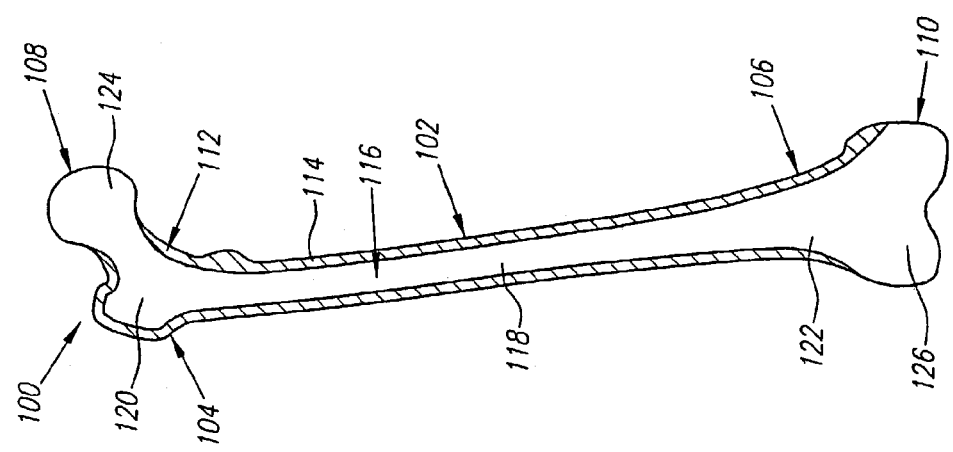

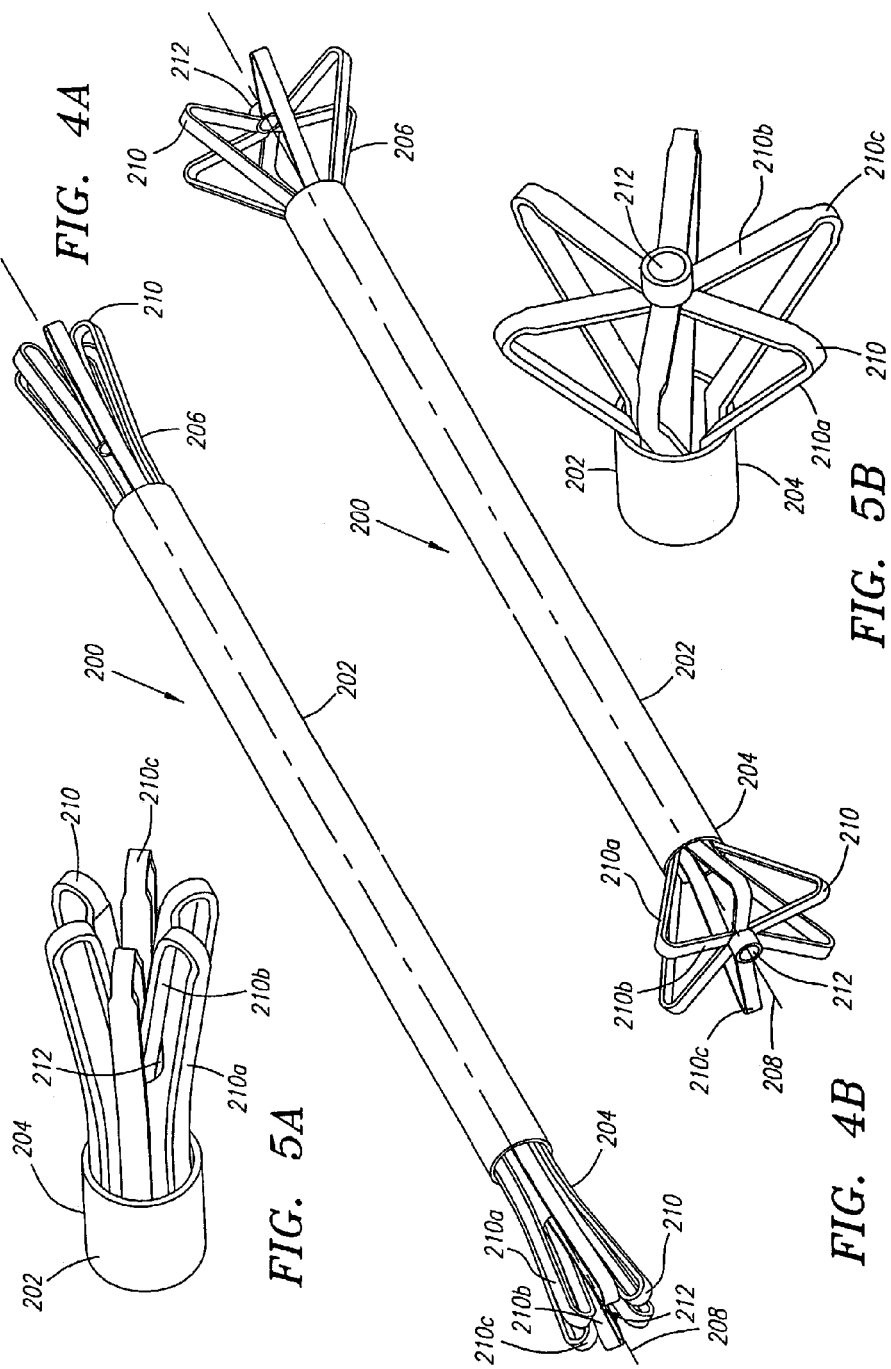

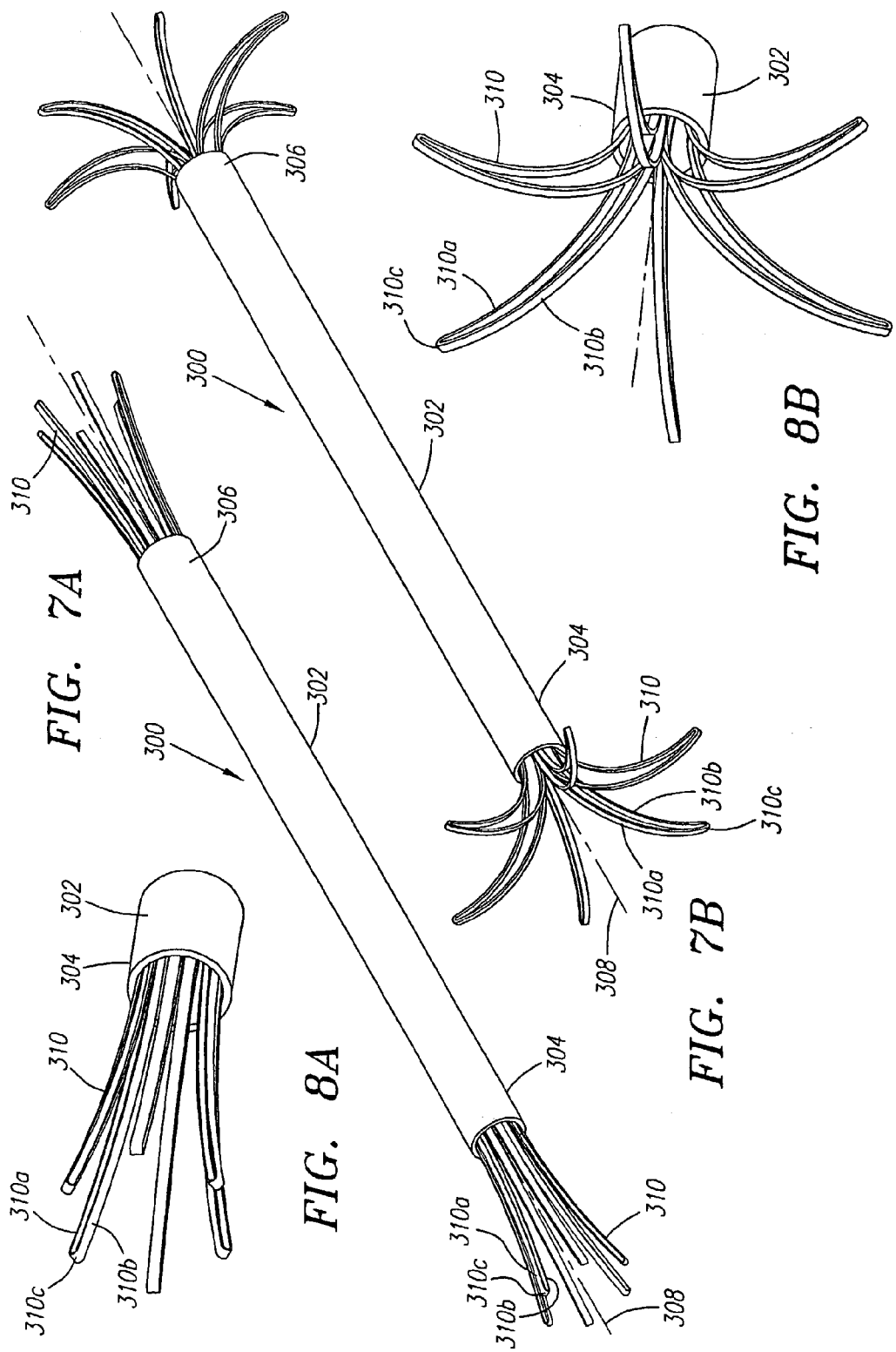

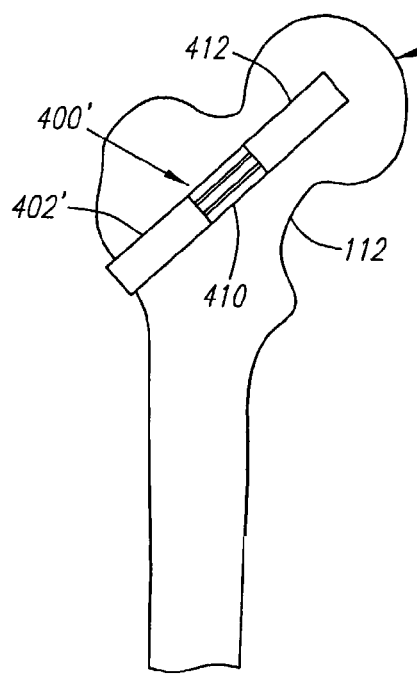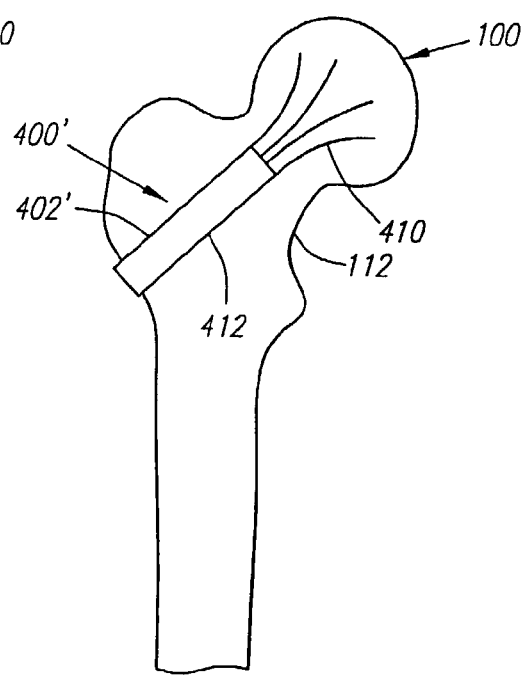
FIG. 10A      FIG. 10B
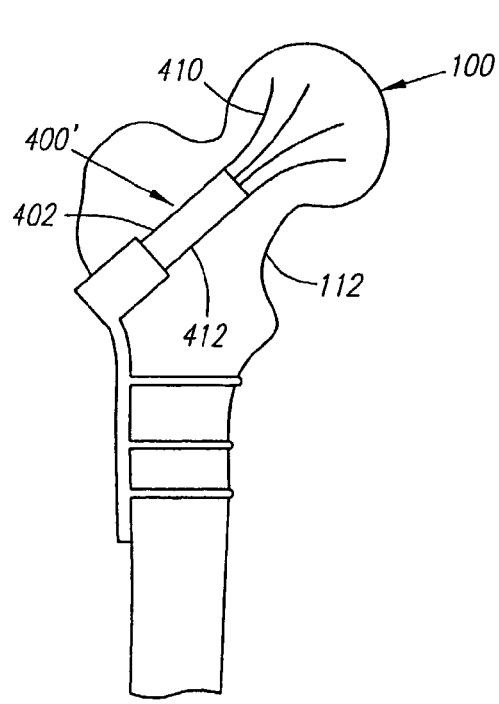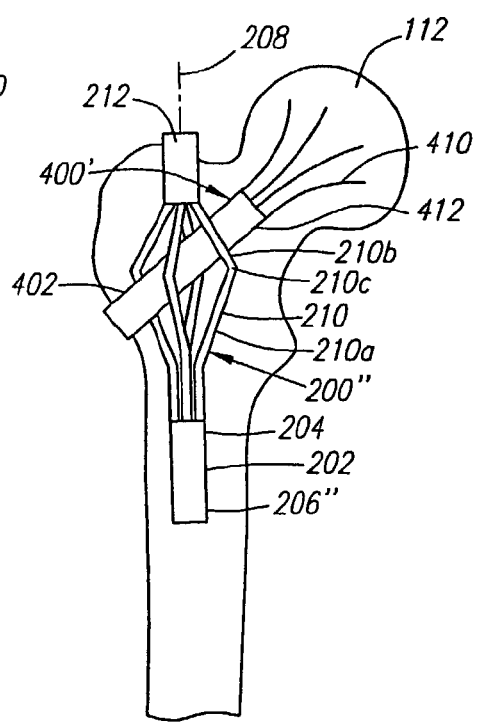
FIG. 11A      FIG. 11B

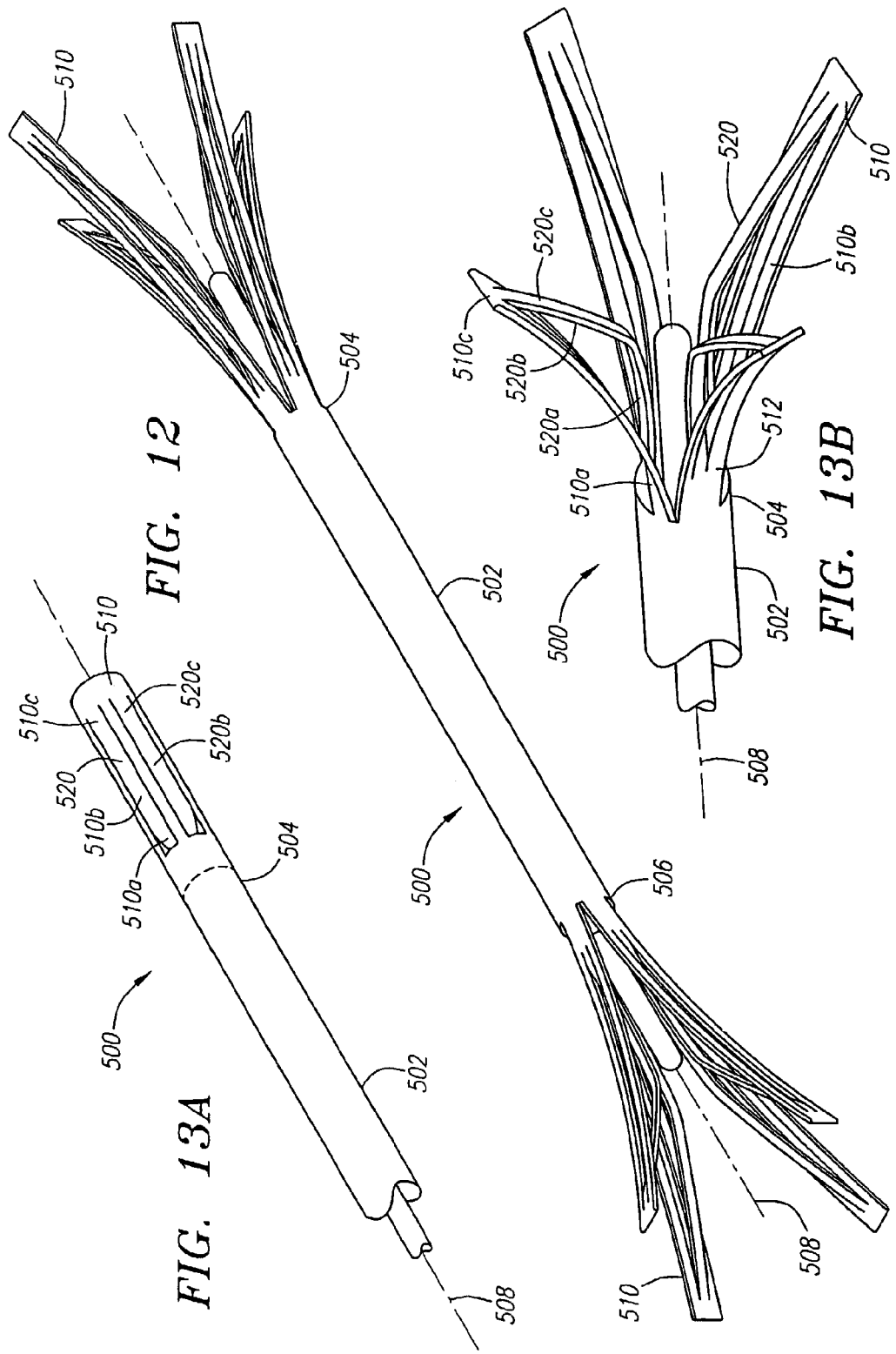

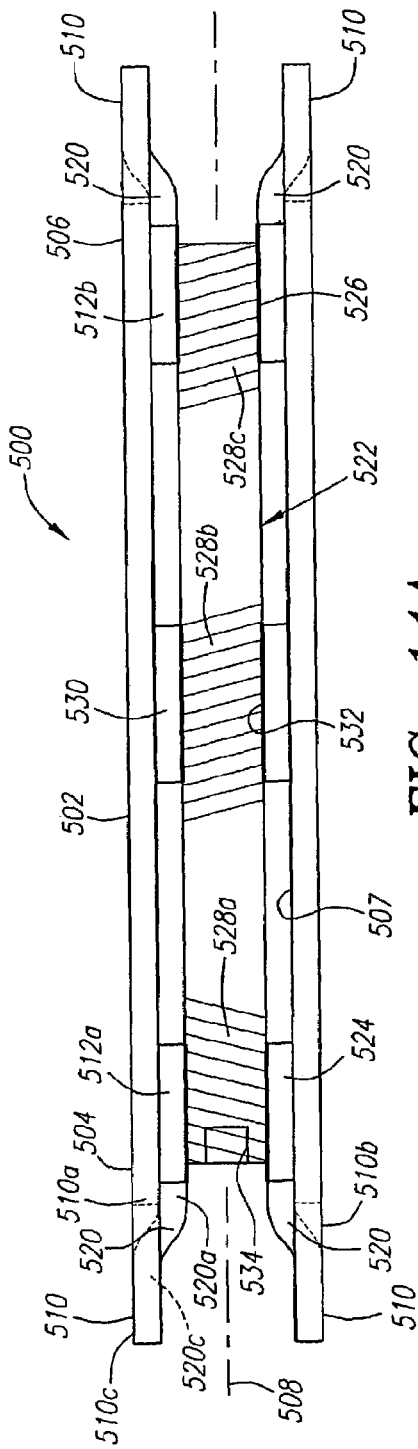
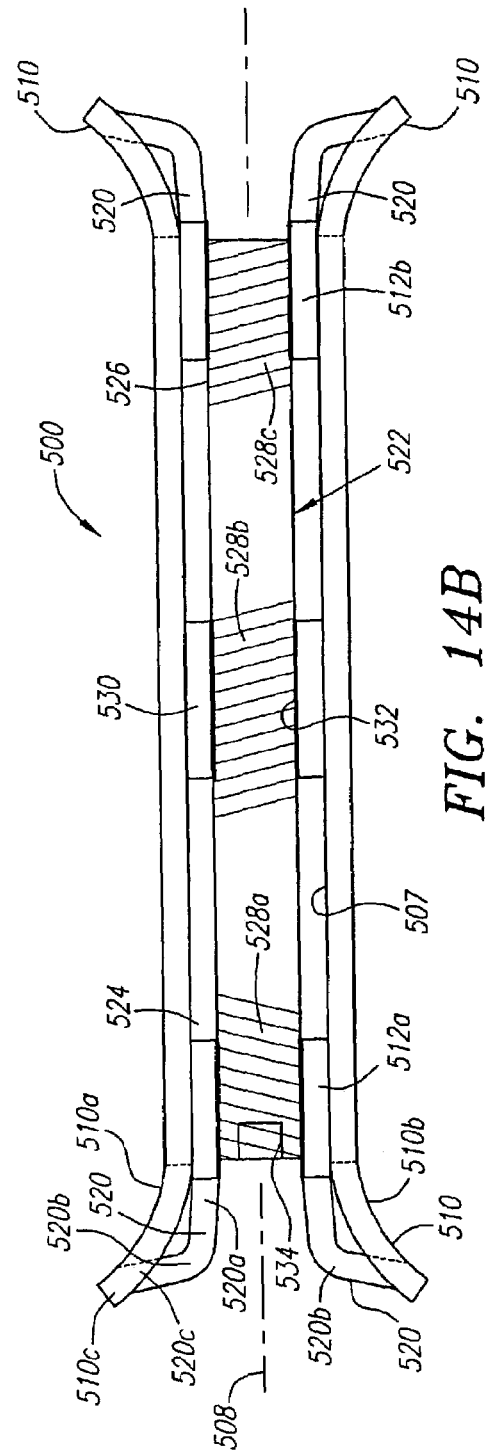

EXPANDABLE ORTHOPEDIC DEVICE

This application is a continuation of U.S. application Ser. No. 09/907,514, filed Jul. 16, 2001, now U.S. Pat. No. 6,554,833, which is a continuation-in part of U.S. application Ser. No. 09/426,563, filed Oct. 22, 1999, now U.S. Pat. No. 6,261,289 on Jul. 17, 2001, which claims benefit of U.S. Provisional Application Ser. No. 60/105,593 filed Oct. 26, 1998, and of PCT Application Serial No. PCT/IL00/00666, filed Oct. 19, 2000 and published on Apr. 26, 2001 as WO 01/28443, the disolosures of which are expressly incorporated herein by reference.

FIELD OF THE INVENTION

The present invention relates to orthopedic devices for surgical treatment of bone fractures and for the prophylactic treatment of pathological bones, and more particularly to expandable intramedullary devices, and to methods for making and using such devices.

BACKGROUND OF THE INVENTION

Fractures of limb bones have been treated with internal fixation devices, such as plates lying on the surface of a bone, nails running inside the medullary canal of a fractured bone, and/or screws affixing both ends of a fractured bone together. These internal fixation devices may provide reasonable structural rigidity and/or stability to the fractured bone without compromising some of the strain desired to stimulate bone cells.

An intramedullary fixation method is a traditional procedure for treating long bone fractures, affixing the bone fracture using intramedullary nails, without disturbing the periosteum of the bone. Such a method may be accomplished in a closed manner, and the fractured bone may be functionally used (including weight bearing) during healing. The surgical approach for insertion of intramedullary nails varies slightly for each bone and is well described in the orthopedic literature.

Some of the problems associated with conventional intramedullary fixation methods include lack of rotation stability, collapse of the fracture site in some fracture types, and/or undesired backup of nails. Furthermore, although the actual shape of the bone typically includes some degree of curvature, the intramedullary nails used to mend the fractured bone are generally straight. Still further, intramedullary fixation methods may introduce interlocking screws across the nail, creating some disadvantages. Specifically, conventional intramedullary fixation nails for long bones may include a rigid structure (hollow or full), that may be locked at their extremes by the addition of screws transversally applied through the bone walls and the nail itself. This additional step generally makes the operation longer and more complicated, and may require additional skin incisions and/or longer use of an image intensifier (X-ray). Furthermore, undesired gaps between the bone ends may originate from the screws, which are permanent unless removed in a new operation. Also, the resultant structure in certain situations may be too stiff and may lack desired elasticity. In contaminated fractures, metallic intramedullary nails may propagate contamination through the entire canal, despite attempts at cleaning the fracture site, which may lead to bone infection.

Recent developments in the intramedullary fixation approach have attempted to address some of these problems. For example, PCT Publication No. WO 98/38918 to Beyar suggests three structural designs: (1) a solid metal sheet that expands in the medullary canal; (2) a meshwork structure consisting of ribs circumferentially connected at the tips; and (3) a balloon structure that is inflated once inserted into the medullary canal. The first two structures, however, may not provide firm support within the metaphysis of the bone. Specifically, these structures are unable to expand at their ends, because the total expansion of the structures is limited by the circumference of the diaphyseal segment of the medullary canal. The balloon structure also has limited utility because, when inflated, it may disrupt blood supply of the bone and prevent regeneration or recovery, and/or may not be adjustable to changes in the shape of the medullary canal, because of its set volume once inserted and inflated.

U.S. Pat. No. 5,281,225 to Vicenzi discloses a structure that includes a multitude of elastically deformable stems connected together by a stub. When inserted in the medullary canal of a fractured bone, the distal tips of the stems expand outward into the end of the medullary canal to anchor the Vicenzi structure within the bone. This device, however, is a passive device, expanding automatically upon deployment, and may not be controllably expanded. Additionally, the Vicenzi structure is not expanded within the medullary canal and, thus, does not provide multiple points of contact with the wall of the medullary canal. As a result, the Vicenzi structure may not ensure structural stability along the transversal and rotational planes of the fractured bone.

Accordingly, intramedullary devices that provide and/or ensure stability to a fractured bone would be considered useful.

SUMMARY OF THE INVENTION

The present invention is directed to orthopedic devices for surgical treatment of bone fractures and for the prophylactic treatment of pathological bones, and more particularly to expandable intramedullary devices, and to methods for manufacturing and implanting them.

According to a first aspect of the present invention, a device for stabilizing bone includes an elongate body having first and second end regions defining a longitudinal axis therebetween. A plurality of splines extend from the first end region, the splines including first ends coupled to the first end region of the elongate body, and second ends disposed away from the first end region, the second ends of the splines being directable from a generally axial collapsed state to a substantially transverse expanded state. Support arms are coupled to the splines, and an actuator is coupled to the support arms, the actuator movable axially relative to the elongate body for causing the support arms to direct the second ends of the splines from the collapsed state to the expanded state.

In one embodiment, the elongate body is a tubular shaft including a lumen extending between the proximal and distal end regions, and the actuator includes an elongate member received within the lumen, and preferably slidably coupled to the tubular shaft by mating threaded regions. A collar is coupled to the elongate member and to the support arms. Preferably, the elongate member includes a threaded region over which the collar is threaded such that rotation of the elongate member relative to the tubular shaft causes the collar to move axially, thereby causing the support arms to direct the splines between the collapsed and expanded states.

In accordance with another aspect of the present invention, a device for stabilizing bone includes an elongate body having first and second end regions defining a longitudinal axis therebetween, and an intermediate region between the first and second end regions. A first plurality of splines extend from the first end region, the splines being directable from a generally axial collapsed state to a substantially transverse expanded state. A second plurality of splines extend from a region of the elongate body distal to the proximal end region, the splines being directable from a generally axial collapsed state to a substantially transverse expanded state.

First and second pluralities of support arms are coupled to the first and second plurality of splines, respectively, and an actuator is coupled to the support arms. The actuator is movable axially relative to the elongate body for causing the first and second pluralities of support arms to direct the splines between the collapsed and expanded states.

Preferably, the elongate body is a tubular shaft including a lumen extending between the proximal and distal end regions, and the actuator includes an elongate member received within the lumen. First and second collars are coupled to the elongate member and to the first and second pluralities of support arms, respectively. Rotation of the elongate member relative to the tubular shaft causes the first and second collars to move axially, thereby causing the first and second pluralities of support arms to direct the splines between the collapsed and expanded states.

In one embodiment, the second plurality of splines extend distally from the distal end region of the tubular shaft. The elongate member may include first and second threaded regions having thread patterns that are opposite hand relative to one another. The first and second collars are threadably coupled to the first and second threaded regions, respectively. Because of the opposite hand thread arrangement, rotation of the elongate member may cause the collars to move in opposite directions. Thus, rotating the elongate member in a first direction may cause the collars to move away from one another to expand the splines, while rotating the elongate member in the opposite direction may cause the collars to move towards one another and collapse the splines.

In an alternative embodiment, the second plurality of splines may be located on the intermediate region of the tubular shaft. In a further alternative, additional sets of splines may be located along the tubular shaft in addition to those described above. Thus, a single actuator may be used to expand multiple sets of splines on a single device. The splines may have differing shapes and/or lengths, thereby enabling the device to be implanted within a bone cavity having a predetermined shape.

Optionally, an axial extension may be provided in a device in accordance with the present invention, e.g., extending proximally from the proximal end of the device beyond the splines. For example, the elongate member may be extended proximally beyond the splines on the first end of the tubular shaft, or the tubular shaft itself may include an extension. Holes may be provided in the axial extension through which nails, screws, or other fixation elements may be received to provide additional transverse support. In a further option, an indicator element may extend proximally from the device or the elongate member may be extended to facilitate location of the device after implantation.

In accordance with yet another aspect of the present invention, a method is provided for making a device for stabilizing bone. An elongate tubular shaft is provided including first and second end regions defining a longitudinal axis therebetween. Splines are formed having first ends remaining attached to the first end region of the tubular body and second ends disposed axially relative to the first ends, the second ends being freely movable relative to the tubular body. Preferably, the splines are formed by creating longitudinal slots in the first end region. Support arms are formed in the splines, the support arms having first ends that are freely movable relative to the splines and second ends remaining attached to the splines. Preferably, the support arms are formed by partially cutting away portions of respective splines.

The first ends of the support arms may be coupled to an actuator, and the actuator may be movable axially relative to the tubular shaft for buckling the support arms transversely outward relative to the longitudinal axis, thereby directing the second ends of the splines transversely outward. In a preferred embodiment, the actuator includes an elongate member and a first collar. The elongate member may be inserted into an axial lumen in the tubular shaft, and the first collar may be threaded over the elongate member until the collar is proximate the first ends of the support arms. The first ends of the support arms may then be coupled to the first collar.

In a preferred embodiment, the tubular shaft includes an internal threaded portion within the lumen, and the elongate member also includes a mating threaded region that slidably engages the threaded portion of the tubular shaft. Thus, axial movement of the elongate member relative to the tubular shaft may be limited except upon controlled rotation of the elongate member.

Optionally, a second set (or additional sets) of splines and support arms may be formed on other regions of the tubular shaft, e.g., on one of the second end region or an intermediate region of the tubular shaft. In this case, a second collar may be threaded over the elongate member until the second collar is proximate the second set of support arms, and the second set of support arms coupled to the second collar.

A device in accordance with the present invention may be inserted through an entry portal previously formed using conventional procedures, e.g., into a medullary canal of a bone, such as the femur, with the splines collapsed. Preferably, a guidewire is first introduced through the entry portal into the medullary canal of the bone using conventional methods and extended to a distal segment of the bone. The device may then be advanced over the guidewire into the medullary canal. After insertion of the device, the guidewire may be removed.

Once the device is fully inserted within the medullary canal, the actuator may be activated, e.g., using a tool inserted into the entry portal, to expand the splines to the expanded state such that the splines substantially engage internal bone or other tissue, thereby substantially anchoring the device relative to the bone. Thus, the device may prevent segments of a fractured bone within which the device is implanted from moving axially, bending, and/or rotating relative to one another. Optionally, if additional stability is desired, an extension may be provided that extends beyond the splines, and fixation devices, e.g., screws or nails, may be introduced transversely into the bone, and through holes in the extension to further secure the segments of bone.

After the fracture has healed, the device may be removed using conventional access procedures. During such removal, a tool may be introduced to activate the actuator and direct the splines back to the collapsed state before removal from the bone.

Other objects and features of the present invention will become apparent from consideration of the following description taken in conjunction with the accompanying drawings.

BRIEF DESCRIPTION OF DRAWINGS

FIGS. 1–3 are sectional side views of a femur, a tibia, and a humerus, respectively.

FIGS. 4A and 4B are perspective views of a first embodiment of an intramedullary device in accordance with the present invention, with splines in collapsed and expanded states, respectively.

FIGS. 5A and 5B are perspective views of one end of the device of FIGS. 4A and 4B, showing splines on the end in collapsed and expanded states, respectively.

FIGS. 7A and 7B are perspective views of a second embodiment of an intramedullary device in accordance with the present invention, with splines in collapsed and expanded states, respectively.

FIGS. 8A and 8B are perspective views of one end of the device of FIGS. 7A and 7B, showing splines on the end in collapsed and expanded states, respectively.

FIGS. 10A, 10B, 11A, and 11B are cross-sectional views of a femur including a fracture being stabilized by alternative embodiments of intramedullary devices, in accordance with the present invention.

FIG. 12 is a perspective view of a fourth preferred embodiment of an intramedullary device in accordance with the present invention, with splines in an expanded state.

FIGS. 13A and 13B are perspective views of one end of the device of FIG. 12, showing the splines in a collapsed state and the expanded state, respectively.

FIGS. 14A and 14B are cross-sectional side views of the device of FIGS. 12 and 13, showing the splines in collapsed and expanded states, respectively.

DETAILED DESCRIPTION OF THE DRAWINGS

Figure 6A:
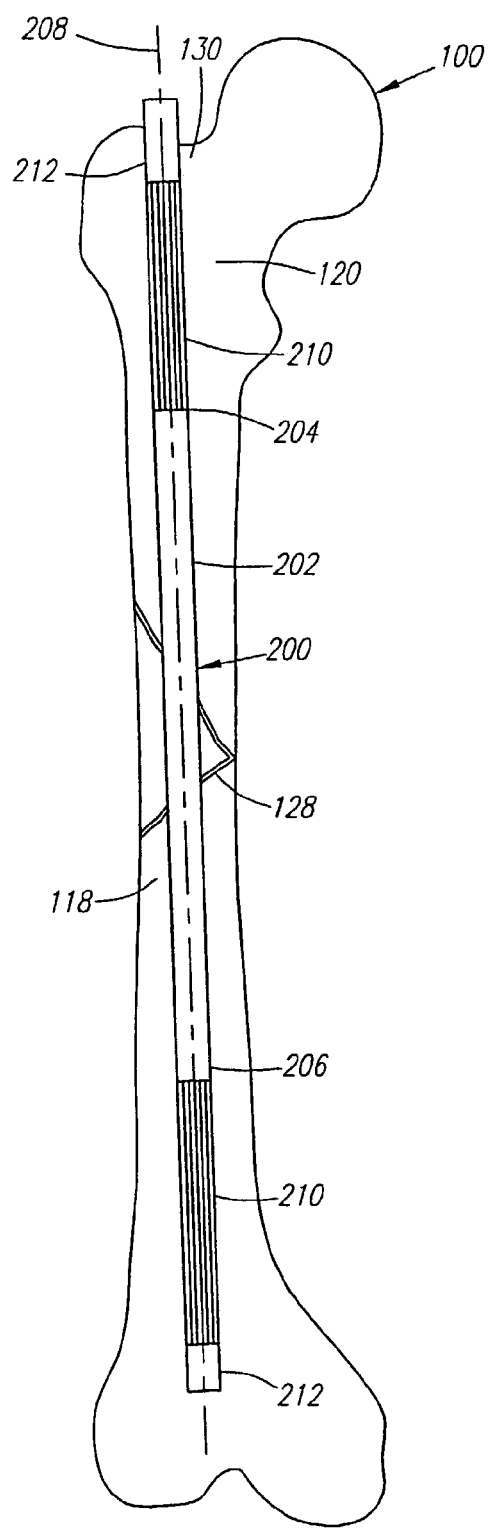
FIGS. 6A and 6B are cross-sectional views of a femur including a fracture being stabilized by the device of FIGS. 4A and 4B.

The present invention may be employed to mend a variety of fractured bones, such as the femur, tibia, or humerus. By way of background the pertinent features of these bones will be described with reference to FIGS. 1–3. Referring specifically to FIG. 1, a femur 100 may be divided into six anatomical regions: a diaphysis or midshaft 102, proximal metaphysis 104, distal metaphysis 106, proximal epiphysis or head 108, distal epiphysis 110, and femoral neck 112. The femur 100 is composed of a hard cortex 114 and a medullary cavity 116. For the purposes of this invention, the medullary cavity 116, includes a medullary canal 118, which runs through the center of the shaft 102, as well as proximal and distal metaphyseal areas 120 and 122, and proximal and distal epiphyseal areas 124 and 126.

Referring specifically to FIG. 2, a tibia 140 may be divided into five anatomical regions: a diaphysis or midshaft 142, a proximal metaphysis 144, distal metaphysis 146, proximal epiphysis 148, and distal epiphysis 150. Like the femur 100, the tibia 140 is composed of a hard cortex 152 and a medullary cavity 154. For the purposes of this specification, a medullary cavity 154 includes a medullary canal 156, which runs through the center of the shaft 142, as well as proximal and distal metaphyseal areas 158 and 160, and proximal and distal epiphyseal areas 162 and 164.

Referring to FIG. 3, a humerus 170, like the tibia 140, maybe divided into five anatomical regions: a diaphysis or midshaft 172, proximal metaphysis or neck 174, distal metaphysis 176, proximal epiphysis or head 178, and distal epiphysis 180. Like the femur 100 and tibia 140, the humerus 170 is composed of a hard cortex 182 and a medullary cavity 184. For the purposes of this specification, a medullary cavity 184 includes a medullary canal 186, which runs through the center of the shaft 172, as well as proximal and distal metaphyseal areas 188 and 190, and proximal and distal epiphyseal areas 192 and 194.

It should be emphasized that the femur 100, tibia 140, and humerus 170 represent exemplary bones in which devices of the present invention may be employed. The present invention maybe used to mend fractured bones, other than the femur 100, tibia 140, and humerus 170, without straying from the scope of the present invention.

Although the medullary canals of the femur 100, tibia 140, and humerus 170 have a generally uniform circumference along the shafts of these bones, the medullary canals are in communication with larger metaphyseal and epiphyseal areas. Thus, the medullary cavities of the femur 100, tibia 140, and humerus 170, as a whole, have a differential circumference, with the circumference at the ends being greater than the circumference at the middle of these medullary cavities. The intramedullary devices of the present invention may be reversibly expanded, e.g., to adopt a pre-formatted shape, fitting the internal shape of the medullary cavity. Use of the intramedullary devices of the present invention may rotationally lock the bone segments of a fractured bone, while at the same time providing sufficient stability in the other planes without the necessity of screws. If screws are needed, they may be used in conjunction with the intramedullary devices. These devices are minimally invasive, and may be implanted through a single incision, the entry portal. Different lengths and types of the intramedullary devices may be necessary, depending upon the bone to be fixed. The intramedullary devices may accommodate a variety of bone circumferences.

The intramedullary devices may be deployed using methods similar to those used for conventional intramedullary nails for bones, such as the femur, tibia and humerus, while minimizing the X-rays needed after the close reduction of the fracture and control of insertion. The intramedullary devices may also be deployed in the radius and ulna through standard approaches used for the insertion of Rush-type nails. For immature bones (with open physis), the intramedullary devices may be inserted through entry portals below the proximal physis and above the distal physis, without including them in the area of fixation. A long intramedullary device may be used, for instance, in knee fusion cases including the femur and tibia. A short intramedullary device may be used, for instance, with metatarsal and metacarpal bone fractures.

This intramedullary approach, along with the minimally invasive nature of the intramedullary devices, generally leaves the periosteum of the fractured bone untouched. In addition, the intramedullary devices may be lighter without compromising the stability, allow better visualization on follow up X-rays due to less metal, and are compatible with the use of other types of externally biomechanic stimuli that could be potentially used as union enhancement treatment. Using certain alloys, the material in which the intramedullary devices are constructed from may remain non-magnetic, avoiding interference with most modern imaging techniques, such as MRI (magnetic resonance imaging).

Turning to FIGS. 4 and 5, a first preferred embodiment of an intramedullary device 200 is shown that includes a tubular shaft 202, and proximal and distal ends 204, 206 defining a longitudinal axis 208 therebetween. The tubular shaft 202 is a generally tubular body, e.g., having a circular or other cross-section. The tubular body may have a solid wall or may have a lattice or other pattern of holes (not shown) formed therein, e.g., for facilitating fluid flow therethrough, for minimizing weight, for providing a desired flexibility, and/or for allowing expansion of the tubular shaft 202. In an alternative embodiment, the tubular shaft 202 may include a plurality of axial spine elements interconnected by a mesh or other interconnecting structure, similar to the embodiments shown and described in application Ser. No. 09/426,563, incorporated by reference herein.

A plurality of splines 210 extend from the proximal end 204 and preferably from both the proximal and the distal ends 204, 206 of the tubular shaft 202, as shown. The splines 210 are expandable between a generally axial collapsed state (shown in FIGS. 4A and 5A) and a substantially transverse expanded state (shown in FIGS. 4B and 5B). The splines 210 may be substantially flat bands, as shown, round wires, filaments, or other structures capable of assuming the collapsed and expanded states.

As best seen in FIGS. 5A and 5B, each of the splines 210 includes a first end region 210a coupled to the tubular shaft 202 and a second end region 210b coupled to a collar 212. The end regions 210a, 210b of the splines 210 may be connected to the tubular shaft 202 and collar 212, for example, by hinged joints (not shown). Alternatively, the end regions 210a, 210b may be integrally formed with the tubular shaft 202 and/or collar 212, and may be sufficiently flexible to bend as needed to accommodate movement between the collapsed and expanded states. Thus, for example, the tubular shaft 202, splines 210, and collars 212 may be formed from a single section of tubing with appropriate material removed using conventional methods to form the splines 210, as will be appreciated by those skilled in the art.

Each spline 210 also includes an intermediate region or loop 210c that may be directed substantially transversely outward with respect to the longitudinal axis 208 to define the expanded state. In the collapsed state, best seen in FIG. 5A, the first and second end regions 210a, 210b of the splines 210 are generally disposed adjacent one another and extend substantially parallel to the longitudinal axis 208. The collar 212 preferably has a diameter substantially smaller than a diameter of the tubular shaft 202 such that the collar 212 may be disposed within the splines 210 in the collapsed state. Thus, the intermediate regions 210c are generally coextensive with the cross-section of the tubular shaft 202 in the collapsed state.

In the expanded state, best seen in FIG. 5B, the collar 212 is displaced axially, i.e., away from the tubular shaft 202. This action displaces the second end regions 210b, thereby causing the intermediate regions 210c of the splines 210 to move substantially transversely outward. Thus, in the expanded state, the splines 210 define a diameter that is substantially greater than the diameter of the tubular shaft 202.

Figure 6B:
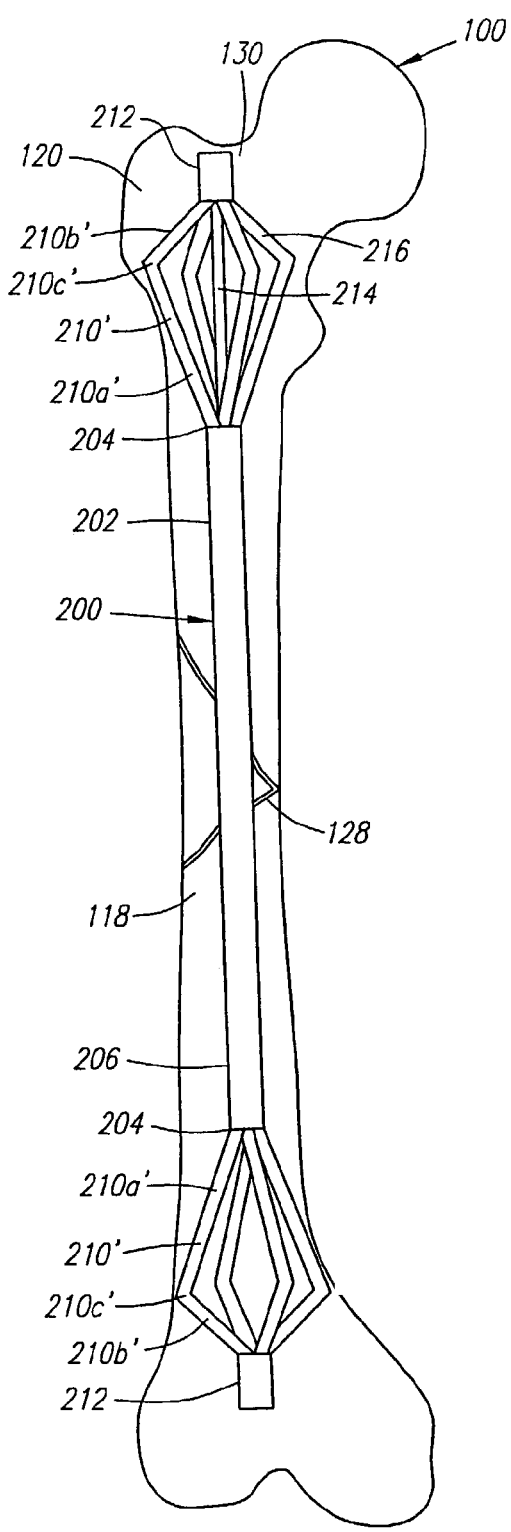

In an alternative embodiment, shown in FIGS. 6A and 6B, the splines 210' may include first and second end regions 210a', 210b' and intermediate regions 210c' that are substantially linear in the collapsed state (FIG. 6A). The first end regions 210a' are coupled to the tubular shaft 202 and the second end regions 210b' are coupled to a collar 212. The collar 212 may be displaced axially, i.e., towards the tubular shaft 202, thereby causing the intermediate regions 210c' to buckle and move substantially transversely outward until they achieve the expanded state (FIG. 6B). The splines 210' may include scored or thinned regions (not shown) to provide hinges or otherwise ensure that the splines buckle in a predetermined manner, i.e., such that the intermediate regions 210c' move substantially transversely outward.

To cause controlled movement of the collar 212, and consequently selective expansion and collapse of the splines 210, the collar 212 is connected to an actuator (not shown). The actuator is generally disposed within the tubular shaft 202, and in a preferred embodiment, the actuator includes an elongate control member 214 (partially seen in FIG. 6B) and an actuating collar (not shown) disposed within the shaft 202. The control member 214 may be a solid rod or tubular member having an outer end 216 coupled to the collar 212 and an inner end (not shown) within the tubular shaft 202. The inner end may have a threaded region for cooperating with a mating threaded region on an actuating collar (not shown). As the actuating collar is rotated within the tubular shaft 202, the control member 214 is displaced axially within the tubular shaft 202, thereby displacing the collar 212 coupled to the splines 210. Thus, the actuator, via the collar 212, is coupled to the splines 210 for selectively expanding the splines 210 between the collapsed and expanded states.

Alternatively, the actuator may be a control wire (not shown) that is coupled to the collar 212 and may be pulled, e.g., axially within the tubular shaft 202, to displace the collar 212. In this alternative, the splines 210 may be biased to one of the collapsed and expanded states, which may be overcome by pulling the control wire, e.g., using a tool inserted into the tubular shaft 202. Other variations may be provided for the actuator, such as mechanical, hydraulic, or pneumatic actuators, as will be appreciated by those skilled in the art.

Turning to FIGS. 6A and 6B, the device 200 may be deployed within a medullary canal 118 of a fractured femur 100, e.g., having a compound fracture 128. Alternatively, the device 200 may be deployed in bones other than the femur 100, such as those described above. First, the device 200 may be inserted through a previously formed entry portal 130 into the medullary canal 118 with the splines 210 collapsed, as shown in FIG. 6A. If the control member 214 is tubular, a guidewire or other elongate element (not shown) may first be introduced within the medullary canal 118, and the device 200 may be advanced over the guidewire, i.e., through a lumen (not shown) of the control member 214, to facilitate positioning of the device 200.

Once the device 200 is fully inserted within the medullary canal 118, the guidewire (if used) may be removed, and a tool (not shown) may be directed through the entry portal 130 and into the tubular shaft 202 to engage and activate the actuator within the device 200. For example, the tool may be a drive tool having a rotating head that engages the actuating collar. The drive tool may be manually, pneumatically, and/or electrically driven to rotate the actuating collar, thereby moving the control member 214 axially within the tubular shaft 202, and consequently displacing the collar 212 until the splines 210 on the proximal end 204 are expanded. The expanded splines 210 may be sufficiently flexible and/or resilient to adapt to the proximal metaphyseal area 120. Thus, the splines 210 may firmly engage the walls of the proximal metaphyseal area 120 at a multitude of contact points. This may secure the device 200, and consequently the segments of the fractured bone both axially and/or torsionally with respect to one another.

Preferably, the splines 210 on the distal end 206 are simultaneously expanded when the splines 210 on the proximal end 204 are expanded. Alternatively, the splines 210 on the distal end 206 may be independently expanded by a separate actuator, e.g., using a similar tool and method to that described with respect to the proximal end 204. In a further alternative, an intramedullary device may be provided that includes only a single set of splines, similar to the embodiments shown in FIGS. 10A–11B.

In a further alternative, if desired, the collar 212 adjacent the proximal set of splines 210 may extend further proximally from the splines 210 and one or more holes (not shown) may be provided therein. Screws, nails, or other fixation devices (also not shown) may be inserted transversely through the bone and through these holes, in order to further enhance the stability of the device 200. Similarly, the collar 212 adjacent the distal set of splines 210 may extend distally from the splines 210 and may include one or more holes for receiving other fixation devices therethrough, in addition to or instead of those on the proximal collar 212.

After the fracture has healed, the device 200 may be removed through the entry portal 130. The entry portal 130 may be covered by new bone growth (not shown) may be exposed through a small skin incision. Optionally, the device 200 may include an indicator element (not shown) that may extend from the proximal end 204. If so, the indicator element may be protruding from or buried under the surface of the new both growth. The new bone growth may be removed around the indicator element to expose the entry portal 130. Once located, the device 200 may be collapsed by rotating the actuating collar in a direction opposite to that used to expand the spine elements 210. The device 200 may then be withdrawn from the medullary canal 118, and the entry portal 130 and overlying tissue allowed to heal.

Alternatively, it may be possible to form the device 200 completely or partially from a bioabsorbable material, so that, in some instances, a second operation to retrieve the device 200 may not be necessary, or only a portion of the device 200 may have to be retrieved.

Turning to FIGS. 7 and 8, a second embodiment of an intramedullary device 300 is shown that includes a tubular shaft 302, and proximal and distal ends 304, 306 defining a longitudinal axis 308 therebetween. The tubular shaft 302 is a generally tubular body, e.g., having a circular or other cross-section, similar to the tubular shaft 210 of the device 200 described above.

A plurality of splines 310 extend from the proximal end 304 and preferably from both the proximal and the distal ends 304, 306 of the tubular shaft 302, as shown. The splines 310 are expandable between a generally axial collapsed state (shown in FIGS. 7A and 8A) and a substantially transverse expanded state (shown in FIGS. 7B and 8B). The splines 310 may be substantially flat bands, filaments, or other structures capable of assuming the collapsed and expanded states.

As best seen in FIGS. 7A and 7B, each of the splines 310 includes a first end region 310a coupled to the tubular shaft 302 and a second end region 310b that enters the first end region 310a of the tubular shaft 302. The second end regions 310b of the splines 310 are coupled to an actuator within the tubular shaft 302. The first end regions 310a of the splines 310 may be connected to the tubular shaft 302, for example, by hinged joints (not shown), or alternatively may be integrally formed with the tubular shaft 302, similar to the embodiments described above.

Each spline 310 also includes an intermediate region or loop 310c that may be directed substantially transversely outward with respect to the longitudinal axis 308 to define the expanded state. In the collapsed state, best seen in FIG. 8A, the first and second end regions 310a, 310b of the splines 310 are generally disposed adjacent one another and extend substantially parallel to the longitudinal axis 308, e.g., such that the intermediate regions 310c are generally coextensive with the cross-section of the tubular shaft 302. In the expanded state, best seen in FIG. 8B, the intermediate regions 310c of the splines 310 are disposed substantially transversely outward. Thus, in the expanded state, the splines 310 define a diameter that is substantially greater than the diameter of the tubular shaft 302.

To cause controlled expansion and collapse of the splines 310, an actuator (not shown) is generally disposed within the tubular shaft 302. In a preferred embodiment, the actuator may include a collar (not shown) slidable within the tubular shaft 302 to which the second end regions 310b are connected. The collar may be controllably displaced axially within the tubular shaft 302, e.g., using a threaded collar and/or rod arrangement similar to that described above. Thus, the actuator is coupled to the splines 310 for selectively expanding the splines 310 between the collapsed and expanded states.

In one embodiment, the splines 310 may be biased to assume their expanded states, and the collar may be displaced axially, e.g., away from the splines 310 to pull the second end regions 310b and collapse the splines 310 to their collapsed states. When the collar is moved axially in the opposite direction, e.g., towards the splines 310, the splines 310 may be free to expand to the expanded state.

During use, the device 300 may be deployed within a medullary canal of a fractured bone (not shown), similar to the embodiment described above. The device 300 may be inserted through a previously formed entry portal into the medullary canal with the splines 310 collapsed. Once the device 300 is fully inserted within the medullary canal, a tool (not shown) may be directed through the entry portal and into the tubular shaft 302 to engage and activate the actuator within the device 300, i.e., to expand the splines 310 on the proximal end 304 to their expanded states. The expanded splines 310 may be sufficiently flexible and/or resilient to adapt to the proximal metaphyseal area and/or to substantially firmly engage the walls of the proximal metaphyseal area at a multitude of contact points.

In one embodiment, the splines 310 on the distal end 306 may be simultaneously expanded when the splines 310 on the proximal end 304 are expanded. Alternatively, the splines 310 on the distal end 306 may be independently expanded by a separate actuator, e.g., using a similar tool and method to that described with respect to the proximal end 304. In a further alternative, an intramedullary device may be provided that includes only a single set of splines, similar to the embodiments shown in FIGS. 10A–11B.

After the fracture has healed, the device 300 may be removed, similar to the embodiment described above. During such removal, a tool is generally introduced into the tubular shaft 302 to engage the actuator and collapse the splines 310, similar to the method for expanding the splines 310. In further alternatives, the device 300 may include an indicator element (not shown) to facilitate removal of the device 300, and/or the device 300 may be at least partially composed of a bioabsorbable material, similar to the embodiment described above.

Figure 9A:
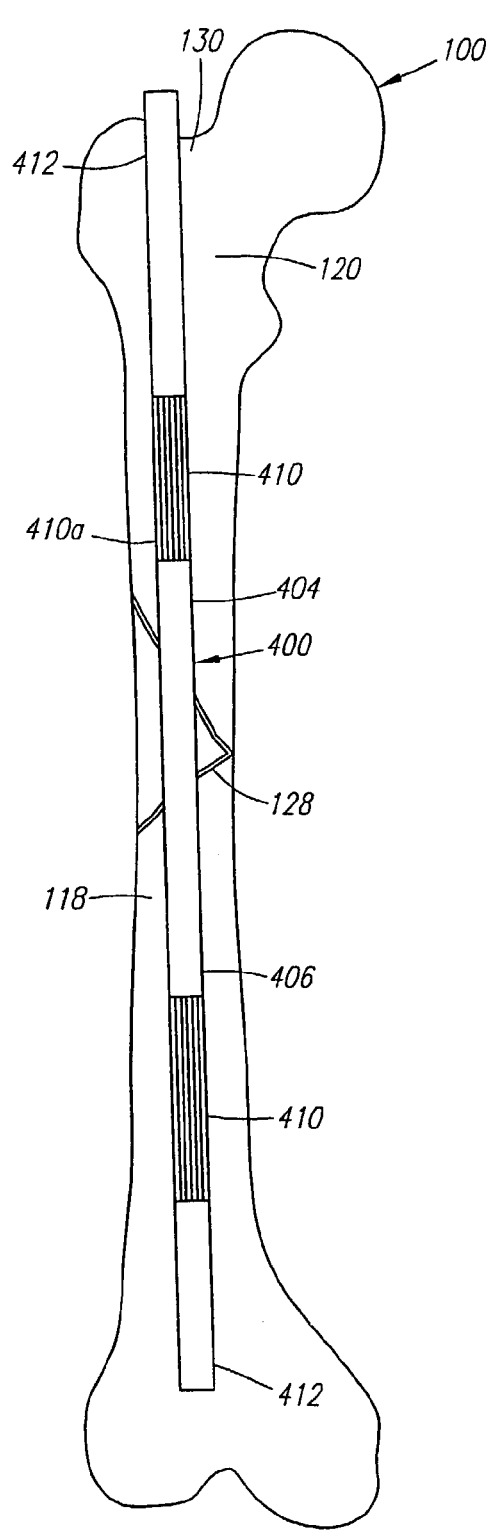
FIGS. 9A and 9B are cross-sectional views of a femur including a fracture being stabilized by a third embodiment of an intramedullary device, in accordance with the present invention.
Figure 9B:
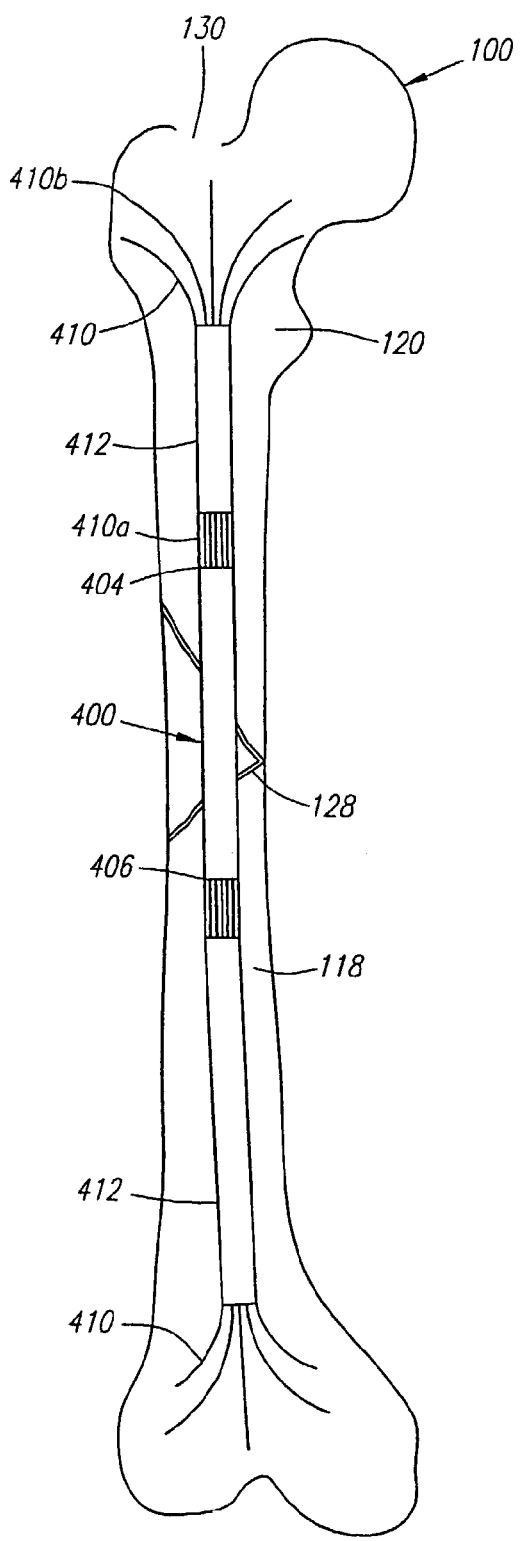

Turning to FIGS. 9A and 9B, another embodiment of an intramedullary device 400 is shown that includes a tubular shaft 402, and proximal and distal ends 404, 406 defining a longitudinal axis 408 therebetween, similar to the embodiments described above. A plurality of splines 410 extend from the proximal end 404 and preferably from both the proximal and the distal ends 404, 406 of the tubular shaft 402, as shown. The splines 410 are expandable between a generally axial collapsed state (not shown) and a substantially transverse expanded state (shown in FIG. 9B). The splines 410 may be substantially flat bands, filaments, or other structures having a first end 410a connected to the tubular shaft 402 and a loose end 410b. Preferably, the splines 410 are biased to assume the expanded state but may be restrained in the collapsed state by overlying sleeves 412, that operates similar to the slidable collars described above.

During use, the device 400 may be deployed within a medullary canal 118 of a fractured femur 100, e.g., having a compound fracture 128. Alternatively, the device 400 may be deployed in bones other than the femur 100, similar to the embodiments described above. The device 400 may be inserted through a previously formed entry portal 130 into the medullary canal 118 with the splines 410 collapsed, as shown in FIG. 9A. Once the device 400 is fully inserted within the medullary canal 118, the sleeves 412 may be directed axially to expose and release the splines 410. Preferably, the splines 210 automatically expand towards the expanded state, and are sufficiently flexible and/or resilient to adapt to the proximal metaphyseal area 120 and/or firmly engage the walls of the proximal metaphyseal area 120.

After the fracture has healed, the device 400 may be removed, similar to the embodiments described above. During such removal, a tool may be introduced to direct the sleeves 412 back over the splines 410, similar to the method for expanding the splines 410. In further alternatives, the device 400 may include an indicator element (not shown) to facilitate removal of the device 400.

Any of the devices described herein may be at least partially composed of a bioabsorbable material, a shape memory alloy or polymer, e.g., Nitinol, or other resilient materials, such as stainless steel or a titanium alloy. In addition, similar to the embodiments shown in FIGS. 10A to 11B, an intramedullary device may include a single set of splines that may be used to stabilize a bone fracture, for example, in or adjacent to a neck or other ends of a bone, such as a femur or humerus, or in a hip bone.

Turning now to FIGS. 12–14B, yet another preferred embodiment is shown of an intramedullary device 500, in accordance with the present invention. Generally, the device 500 includes a tubular shaft 502, one or more collars 512, and an elongate control member 522. The tubular shaft 502 includes proximal and distal ends 504, 506 defining a longitudinal axis 508 therebetween. The tubular shaft 502 is a generally tubular body, e.g., having a circular or other cross-section (e.g., oval, square, fluted, and the like), and defining a lumen 507 extending between the proximal and distal ends 504, 506. The tubular body 508 may have a solid wall or may have a lattice or other pattern of holes (not shown) formed therein, e.g., for facilitating fluid flow therethrough, for minimizing weight, for providing a desired flexibility, and/or for allowing expansion of the tubular shaft 502. In an alternative embodiment, the tubular shaft 502 may include a plurality of axial spine elements interconnected by a mesh or other interconnecting structure, as described in application Ser. No. 09/426,563, incorporated above by reference.

A plurality of splines 510 extend from the proximal end 504 and preferably from both the proximal and the distal ends 504, 506 of the tubular shaft 502, as shown. A plurality of support arms 520 are coupled to the splines 510 for expanding the splines 510 between a generally axial collapsed state (shown in FIGS. 13A and 14A) and a substantially transverse expanded state (shown in FIGS. 13B and 14B). Preferably, the splines 510 and support arms 520 are formed from a single band of material, as explained further below. Alternatively, they may be formed as separate components that are attached to one another, e.g., by welding, bonding, adhering, and the like. In further alternatives, the splines 510 and/or support arms 520 may be substantially round wires, filaments, or other structures capable of assuming the collapsed and expanded states.

As best seen in FIGS. 13A–14B, each of the splines 510 includes a first end region 510a coupled to the tubular shaft 502 and a second free end region 510c located away from the tubular shaft 502. Preferably, the second end region 510c is located substantially axially away from the tubular shaft 502 in the collapsed state. Each respective support arm 520 includes a first end 520a that is coupled to collar 512 and a second end 520c that is coupled to a respective spline 510. Preferably, the second end 520c of the support arm 520 is coupled to the free end region 510c of the spline 510, although alternatively, the second end of the support arm 520 may be coupled to an intermediate region 510b of the spline 510 (not shown).

Preferably, the first end regions 510a of the splines 510 are integrally formed with the tubular shaft 502, while the second ends 520c of the support arms 520 are integrally formed with the second end regions 510a of respective splines 510. The intermediate regions 510b, 520b of the splines 510 and support arms 520 may be sufficiently flexible to bend as needed to accommodate movement between the collapsed and expanded states, as described further below. For example, the tubular shaft 502, splines 510, and support arms 520 may be formed from a single section of tubing with appropriate material removed, as explained further below. Alternatively, the first end regions 510a of the splines 510 may be separate bands connected to the tubular shaft 502 by welded joints, hinges, or pins (not shown), and/or the second ends 520c of the support arms 520 may be connected to the second end regions 510c of the splines 510 by welded joints, hinges, or pins (not shown).

Turning to FIGS. 14A and 14B, the control member 522 may be a solid rod or a tubular member having proximal and distal ends 524, 526. The control member 522 has a diameter or other cross-section such that the control member 522 may be received within the lumen 507 of the tubular shaft 502. Preferably, the control member 522 includes one or more threaded regions, such as a proximal threaded region 528a, intermediate threaded region 528b, and distal threaded region 528c, as shown. More preferably, the proximal and distal threaded regions 528a, 528c have opposite hand threads from one another, which is explained further below.

The tubular shaft 502 may include an internal annular region 530 disposed within the lumen 507 that defines an inner surface 532 that is threaded similar to the intermediate threaded region 528b of the rod 522. The annular region 530 preferably has a diameter similar to the control member 522 such that threads on the inner surface 532 engage the threaded intermediate region 528b to prevent axial movement of the rod 522, except when the rod 522 is rotated about axis 508. The annular region 530 may be machined from the tubular shaft 502 or may be an annular sleeve that is inserted into the lumen 507 and secured at an intermediate location, e.g., by welding, bonding, and the like.

Similarly, the collars 512 also have threaded inner surfaces that may engage the proximal and distal threaded regions 528a, 528c of the control member 522. Preferably, the proximal collar 512a has an internal threaded pattern that is opposite hand to the distal collar 512b for mating with the proximal and distal threaded regions 528a, 528b, respectively. In addition, the collars 512 have an outer diameter such that the collars 512 may be slidably received within the lumen 507 in the proximal and distal ends 504, 506 of the tubular shaft 502. The collars 512 may include slots or pockets (not shown) for receiving the first ends 520a of the support arms 520, as described further below.

With reference to FIGS. 15A–15D, a preferred method is shown for manufacturing the splines 510 and support arms 520 as integral elements of the tubular shaft 502. Although only one end is shown, it will be appreciated that splines 510 and support arms 520 may be formed on both ends, if desired, as described herein. In addition, it will be appreciated that the sequence of the steps to manufacture the tubular shaft 502 is not important and may be completed in any order.

Figure 15A:
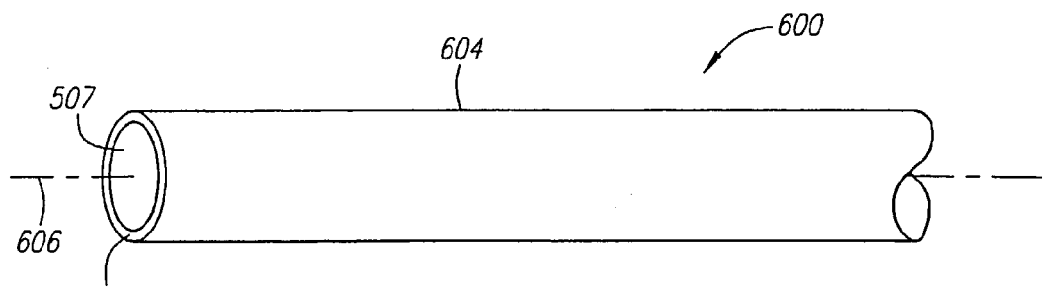
FIGS. 15A–15D are perspective views, showing a method for forming splines in a tubular body, in accordance with the present invention.
Figure 15B:
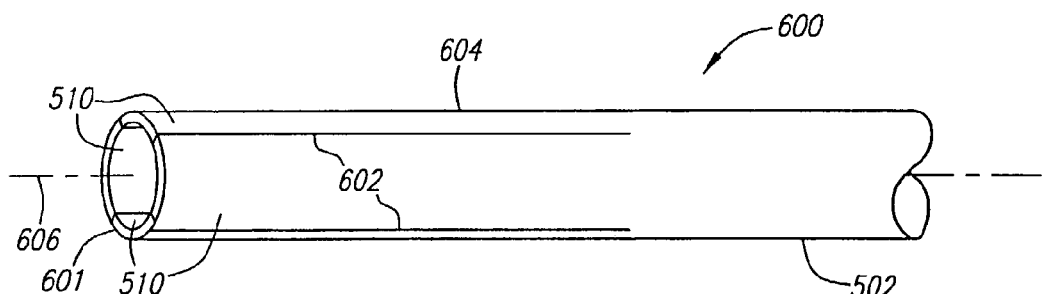

First, as shown in FIG. 15A, an elongate tube 600 is provided, preferably having a cylindrical (or other) shape, that is cut to a length (not shown) corresponding to a combined length of the finished tubular shaft 502 and the splines 510 on one end (or both ends) of the tubular shaft 502. The tube may be formed from a variety of biocompatible materials that provided sufficient structural integrity, with stainless steel or titanium being preferred. First slots 602 may be created in the end(s) 604 of the tube 600 that extend longitudinally substantially parallel to axis 606, thereby defining the splines 510 between adjacent slots 602, as shown in FIG. 15B. The first slots 602 may be formed by laser cutting, mechanical cutting, and the like. If desired, the longitudinal edges defined by the first slots 602 may be rounded, trimmed, or otherwise modified to prevent adjacent splines 510 from catching on one another, e.g., when directed from or back to the collapsed state.

Figure 15C:
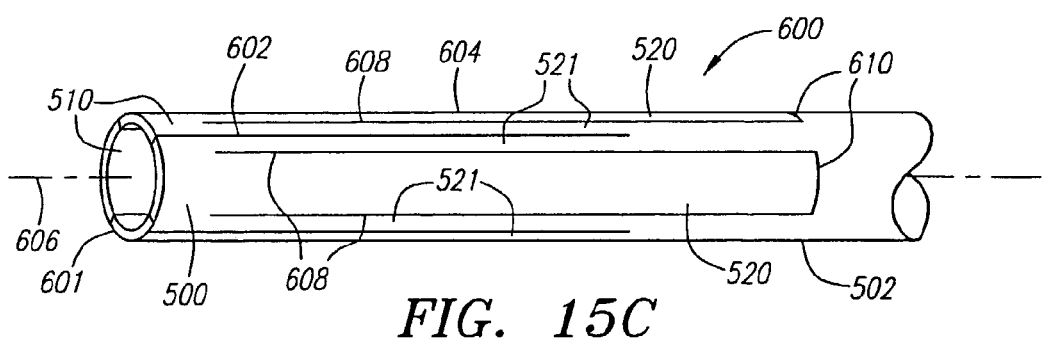

Turning to FIG. 15C, pairs of second slots 608 may be created between adjacent first slots 602 that extend substantially parallel to axis 606 without extending entirely to the end 601 of the tube 600. Ends of the second slots 608 may be connected with circumferential slots 610, thereby defining support arms 520. Thus, each of the splines 520 may be defined by a pair of narrow stems 511 that extend on either side of a respective support arm 520 from the tubular shaft 502 and terminate in a free end 510c. The support arms 520 may be longer than the splines 510, as shown, to provide greater flexibility as compared to the splines 510, or alternatively, the support arms 520 may be generally the same or shorter than the splines 510. It will be appreciated by those skilled in the art that the relative width and length of the splines 510 and support arms 520 may be easily determined to provide a desired extent and ease of expansion and collapse.

Figure 15D:
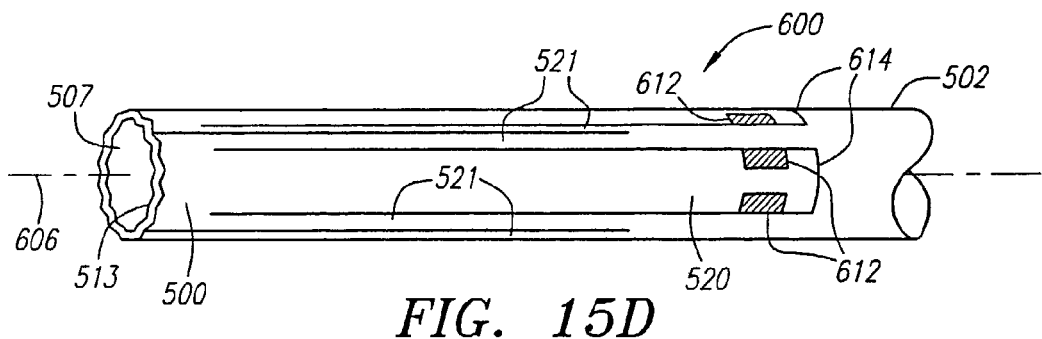

Optionally, as shown in FIG. 15D, the free ends 510c of the splines 510 may be treated to create tissue engaging elements, such as jagged tines 513. Alternatively or in addition, the free ends 510c may be bent or curved, e.g., radially outward (not shown), to enhance engagement with bone or other tissue during implantation. In addition, one or more notches 612 may be formed in a first end 520a of each of the support arms 520 to define tabs 614 for securing the support arms 520 to the collar 512 (not shown). In a further alternative, the splines 510 and support arms 520 may be formed on a separate tubular sleeve that may be attached to one or both ends of a tubular shaft (not shown), e.g., by welding, friction fit, mating threads, bonding, and the like.

Returning to FIGS. 14A and 14B, once the splines 510 and support arms 520 are formed on or attached to one or both ends 504, 506 of the tubular shaft 502, collar(s) 512 may be inserted into the lumen 507 and the first ends 520a of the support arms 520 may be attached to respective collar(s) 512. The collar(s) 512 may include slots or recesses (not shown) for receiving the tabs 614 of respective support arms 520. In addition or alternatively, the first ends 520a of the support arms 520 may be bonded or welded to the collar(s) 512.

Preferably, collar(s) 512 may be threaded over the control member 522 into the tubular shaft 502. The control member 522 may be inserted into the lumen 507 of the tubular shaft 502, and threaded through the annular region 530 until the proximal and distal ends 524, 526 are disposed within the proximal and distal ends 504, 506 of the tubular shaft 506. The collar(s) 512 may be threaded onto proximal end 524 (and/or the distal end 526) until the collar(s) 512 enter(s) the lumen 507 and become disposed proximate the first ends 520a of the support arms 520. The support arms 520 may then be attached to the collar(s) 512, as described above.

Initially, the device 500 may be provided such that the splines 510 are in their collapsed state, as shown in FIG. 13A. In the collapsed state, the splines 510 and support arms 520 may be disposed adjacent one another such that they extend substantially parallel to the longitudinal axis 508. To expand the splines 510, a tool (not shown) may be used to rotate the control member 522 in a predetermined direction. For example, as shown in FIGS. 14A and 14B, a slot 534 or other keyed element, such as a lug (not shown) extending from the control member 522, may be provided that may be engaged with the tool. Because the thread pattern on the proximal and distal threaded regions 528a, 528c are opposite hand from one another, as the control member 522 is rotated, both collars 512 move outwardly from the lumen 507. Stated differently, the proximal collar 512a moves proximally, while the distal collar 512b moves distally.

This action of the collars 512 causes the first ends 520a of the support arms 520 to move axially outward (i.e., proximally for the support arms 520 on the proximal end 504). Thus, if splines 510 are provided on both the proximal and distal ends 504, 506 of the tubular shaft 502, the first ends 520a of the proximal and distal support arms 520 may away from one another. Because the second ends 520c of the support arms 520 are coupled to the splines 510, this causes intermediate regions 520b of the support arms 520 to buckle and directs the splines 510 radially outward until they are oriented substantially transversely with respect to the longitudinal axis 508 to define the expanded state, as shown in FIG. 12.

Use of the device 500 to treat a fracture within a bone may proceed similar to the embodiments described above. The device 500 may be inserted through a previously formed entry portal into a medullary canal of a bone, such as the femur (not shown) with the splines 510 collapsed, as shown in FIG. 13A. Preferably, a guidewire or other element (not shown) is first introduced through the entry portal into the medullary canal of the bone using conventional methods and extended to a distal segment of the bone. The device 500 may then be advanced over the guidewire into the medullary canal, e.g., by inserted the guidewire through a lumen in the control member 522. After insertion of the device 500, the guidewire may then be removed.

Once the device 500 is fully inserted within the medullary canal, the control member 522 may be rotated to expand the splines 510 to the expanded state, as shown in FIG. 13B. Preferably, the splines 510 are expanded such that they substantially engage internal bone or other tissue, thereby substantially anchoring the device 500 relative to the bone. Thus, the device 500 may prevent segments of bone within which the device 500 is implanted from moving axially, bending, and/or rotating relative to one another. Optionally, if additional stability is desired, a proximal extension (not shown) may be provided that extends proximally beyond the splines 510 on the proximal end 504. For example, the tubular shaft 502 may include an axial extension (not shown) that extends proximally beyond the splines 510 (which may require elimination of one or more of the splines 510 to accommodate the extension), or alternatively the control member 522 may extend proximally beyond the splines 510. A plurality of holes (not shown) may be provided through the proximal extension, and screws, nails, or other fixation devices may be inserted through the holes, e.g., transversely through the bone and the proximal extension, to further secure the segments of bone.

An advantage of the threading of the control member 522 is that it allows the splines 510 on one end of the device 500 to be expanded to a greater size than the splines 510 on the other end. Rather than merely rotating the control member 522, which may cause each set of splines 510 to expand substantially equally to one another, an axial force may be applied to the control member 522, causing the control member 522 to move axially through the tubular shaft 502. Thus, rather than the collars 512 moving relative to the tubular shaft 502, one collar 512 may remain substantially stationary, while the other collar 512 moves further outwardly.

After the fracture has healed, the device 500 may be removed, similar to the embodiments described above. During such removal, a tool may be introduced to direct the splines 510 back to the collapsed state, similar to the method for expanding the splines 510. In further alternatives, the device 500 may include an indicator element (not shown) to facilitate location and/or removal of the device 500.

Figure 16:
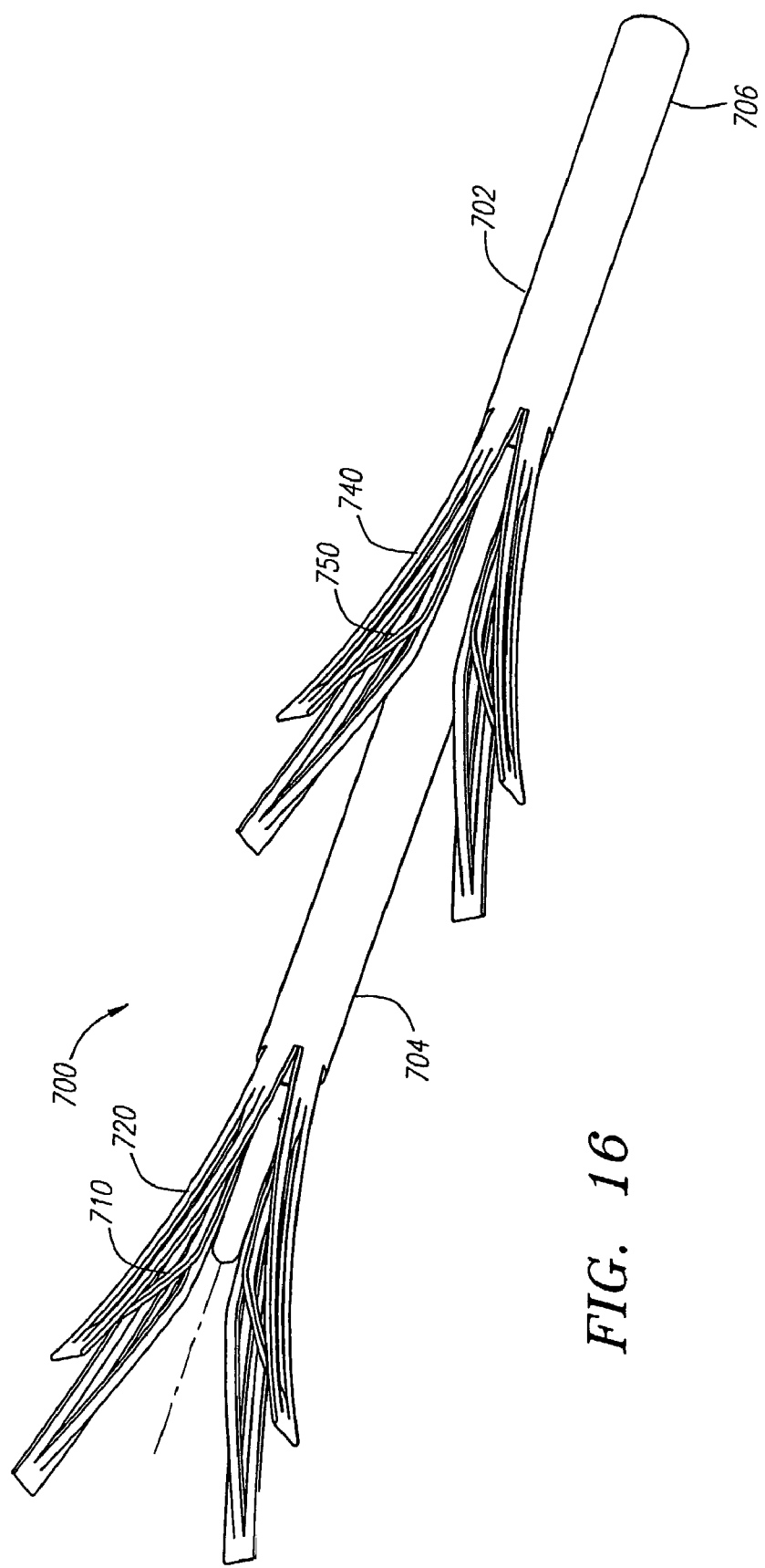
FIG. 16 is a perspective view of an alternative embodiment of an intramedullary device, in accordance with the present invention.

Turning to FIG. 16, an alternative embodiment of an intramedullary device 700 is shown that includes a first set of splines 710 on one end 704 of a tubular shaft 702, similar to the previously described embodiment. In addition, the device 700 includes a second set of splines 740 that are located at an intermediate location between the ends 704, 706 of the tubular shaft 702. The second set of splines 740 includes support arms 750, both of which may be formed directly in a wall of the tubular shaft 702, similar to those formed on the end 704. A collar (not shown) may be inserted into the tubular shaft 702, e.g., threaded over a rod or other control member (also not shown), similar to the previous embodiment until the collar is proximate the second set of splines 740. The support arms 750 may then be coupled to the collar, such that rotation of the rod may cause the collar to move axially and expand the second set of splines 740, similar to the previously described embodiment. Optionally, a plurality of holes (not shown) may be provided through the tubular shaft 702. Screws, nails, or other fixation devices may be inserted through the holes, e.g., transversely through the bone and the shaft, to further secure the segments of bone, similar to the embodiment described above.

Although only one set of intermediate splines 740 is shown, it will be appreciated that any number of sets of splines may be provided along the tubular shaft in a similar manner. Thus, when the device 700 is implanted within a long bone, the device 700 may be expanded to engage several locations of the bone along its length. In addition, although the first and second sets of splines 710, 740 are shown as having substantially the same length, it will be appreciated that different length splines may be provided. For example, the intermediate set of splines may be made shorter than those on the end(s), e.g., to allow expansion within a narrow region of a bone, while the set(s) of splines on the end(s) may expand within an enlarged region, e.g., end(s) of the bone.

In a further alternative, the devices in accordance with the present invention may be used as a base for an intramedullary primary fixation stem prosthetic section. For example, an adapter (not shown) may be attached to the device, e.g., to the tubular shaft proximal or distal to the set of splines to which a prosthetic artificial joint surface, e.g., a rounded component, socket or other joint element (also not shown), may be attached. Alternatively, a prosthesis may be secured directly over the set of splines. Thus, the devices may be used in joint replacement procedures in addition to or instead of merely stabilizing a fractured bone.

While preferred methods and embodiments have been shown and described, it will be apparent to one of ordinary skill in the art that numerous alterations may be made without departing from the spirit or scope of the invention. Therefore, the invention is not to be limited except in accordance with the following claims.

What is claimed is:

1. A device for stabilizing bone, comprising:
an elongate body having first and second end regions defining a longitudinal axis therebetween;
a plurality of splines extending from the first end region, the splines being directable from a collapsed state to a substantially transverse expanded state;
a plurality of support arms coupled to the splines; and
an actuator coupled to the support arms, the actuator movable axially relative to the elongate body for displacing distal ends of the support arms away from the longitudinal axis, thereby causing the splines to bend in a curvilinear manner away from one another towards the expanded state.

2. The device of claim 1, wherein the splines curve radially outwardly as they are directed towards the expanded state.

3. The device of claim 2, wherein the splines curve back on themselves as they are directed towards the expanded state.

4. The device of claim 1, wherein the support arms are coupled to free ends of the splines, thereby causing the free ends of the splines to bend radially outwardly as they are directed towards the expanded state.

5. The device of claim 4, wherein the free ends of the splines curve back towards the second end region of the tubular member as the splines are directed towards the expanded state.

6. The device of claim 1, wherein the support arms are coupled to intermediate regions of the splines, the intermediate regions buckling as the splines are directed towards the expanded state.

7. The device of claim 1, wherein the support arms are substantially straight in the collapsed state, and wherein the splines and support arms buckle substantially transversely outwardly as they are directed towards the expanded state.

8. The device of claim 1, further comprising a plurality of splines extending from the second end region, the splines being expandable between a collapsed configuration and a substantially transverse expanded configuration.

9. The device of claim 8, wherein the splines on the second end region are coupled to the actuator by supporting arms.

10. The device of claim 1, wherein the elongate body comprises a tubular body, and wherein the splines are formed by cutting longitudinal slots in the first end region of the tubular body.

11. The device of claim 10, wherein the support arms are formed by partially cutting away portions of respective splines such that the support arms define first ends that remain attached to the respective splines and second ends that are coupled to the actuator.

12. The device of claim 1, wherein the elongate body comprises a tubular member comprising a lattice or pattern of holes formed therein.

13. A device for stabilizing bone, comprising:
an elongate body having proximal and distal end regions defining a longitudinal axis therebetween;
a plurality of splines extending from the distal end region, the splines being directable from a collapsed state to a substantially transverse expanded state;
a plurality of support arms coupled to the plurality of splines; and
an actuator coupled to the support arms, the actuator movable relative to the elongate body for causing the support arms to direct the splines between the collapsed and expanded states;
wherein the splines and the support arms are formed from at least a portion of a tubular shaft.

14. The device of claim 13, wherein the splines and the support arms are formed from a distal portion of the tubular shaft.

15. The device of claim 13, wherein the tubular shaft is the elongate body.

16. A device for stabilizing bone, comprising:
an elongate body having first and second end regions defining a longitudinal axis therebetween;
a plurality of splines extending from the first end region, the splines being directable from a collapsed state to a substantially transverse expanded state;
a plurality of support arms coupled to the splines; and
an actuator coupled with at least one of the support arms and including an elongate member, the elongate member being movable axially relative to the elongate body for displacing distal ends of the support arms away from the longitudinal axis, thereby causing the splines to bend away from one another towards the expanded state.

17. The device of claim 16, wherein the elongate body comprises a tubular shaft, and wherein the actuator is coupled with the support arms, the actuator being movable axially relative to the tubular shaft, thereby directing the second ends of the splines substantially transversely outward with respect to the longitudinal axis to define the expanded state.

18. The device of claim 16, wherein the elongate body comprises a tubular shaft including a lumen extending between the first and second end regions, and the actuator includes a connector coupled to the elongate member and to the plurality of support arms, wherein rotation of the elongate member relative to the tubular shaft causes the connector to move axially, thereby causing the plurality of support arms to direct the splines between the collapsed and expanded states wherein the elongate member is received within the lumen.

19. A method for treating a fracture in a bone, comprising:
providing an elongate tubular body including a plurality of splines extending from a distal end of the tubular body, support arms coupled to the splines, and an actuator coupled to the support arms;
inserting the distal end of the tubular body into a passage through bone extending across a fracture in the bone with the splines in a collapsed state;
positioning the actuator distally relative to the tubular body to move the support arms, thereby causing the splines to curve radially outwardly away from one another in a pattern substantially transverse to said elongate tubular body to stabilize the bone.

20. The method of claim 19, wherein the splines comprise free ends that are curved radially outward, the free ends engaging surrounding bone to enhance engagement with the bone.

21. The method of claim 19, wherein the passage comprises a medullary canal within the bone.

22. The method of claim 19, wherein the splines substantially engage bone as the actuator is positioned, thereby substantially anchoring the tubular body relative to the bone.

* * * * *